(12) United States Patent
Ashby et al.

(10) Patent No.: US 8,383,725 B2
(45) Date of Patent: *Feb. 26, 2013

(54) POLYESTER BASED DEGRADABLE MATERIALS AND IMPLANTABLE BIOMEDICAL ARTICLES FORMED THEREFROM

(75) Inventors: Valerie Ashby, Durham, NC (US); David Olson, Minneapolis, MN (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/204,774

(22) Filed: Aug. 8, 2011

(65) Prior Publication Data

US 2012/0027719 A1 Feb. 2, 2012

Related U.S. Application Data

(63) Continuation of application No. 12/281,171, filed as application No. PCT/US2007/005643 on Mar. 5, 2007, now Pat. No. 8,013,061.

(60) Provisional application No. 60/780,250, filed on Mar. 8, 2006.

(51) Int. Cl.
*C08G 63/48* (2006.01)
*C08G 63/66* (2006.01)

(52) U.S. Cl. .......... 525/47; 525/437; 525/445; 528/301; 528/303; 528/306; 424/422; 424/423

(58) Field of Classification Search ........................ None
See application file for complete search history.

(56) References Cited

U.S. PATENT DOCUMENTS

| 4,826,945 | A | * | 5/1989 | Cohn et al. | .................... 424/423 |
| 5,711,958 | A | * | 1/1998 | Cohn et al. | .................... 424/423 |
| 6,583,260 | B2 | | 6/2003 | Sheares | |
| 6,706,854 | B2 | | 3/2004 | Buchholz et al. | |
| 6,773,714 | B2 | | 8/2004 | Dunn et al. | |
| 2004/0019178 | A1 | | 1/2004 | Gross et al. | |
| 2004/0082023 | A1 | | 4/2004 | Gross et al. | |
| 2004/0082024 | A1 | | 4/2004 | Brandstadt et al. | |
| 2004/0156819 | A1 | * | 8/2004 | Cohn et al. | ................. 424/78.38 |
| 2005/0261447 | A1 | | 11/2005 | Koshiro et al. | |

OTHER PUBLICATIONS

International Search Report and Written Opinion, PCT/US07/05643, mailed Sep. 12, 2007.

* cited by examiner

*Primary Examiner* — Ling Choi
*Assistant Examiner* — Gennadiy Mesh
(74) *Attorney, Agent, or Firm* — Myers Bigel Sibley & Sajovec, P.A.

(57) ABSTRACT

A method of making an aliphatic polyester prepolymer, comprising: reacting, alone or in combination with other reactants, a diol with at least a first diacid (or a diester of said first diacid) to produce an aliphatic polyester prepolymer. The first diacid is preferably a trans-beta-hydromuconic acid (HMA). In some embodiments, the diol contains at least one ether linkage. In some embodiments the diol is further reacted with at a second diacid, or a diester of said second diacid, wherein said second diacid is different from said first diacid. Prepolymers produced from such processes and articles formed therefrom are also described.

17 Claims, 5 Drawing Sheets

POLYESTER BASED DEGRADABLE MATERIALS AND IMPLANTABLE BIOMEDICAL ARTICLES FORMED THEREFROM

RELATED APPLICATIONS

This application is a continuation of and claims priority to U.S. patent application Ser. No. 12/281,171, filed Mar. 18, 2009 now U.S. Pat. No. 8,018,061, now allowed, which is a national phase application of PCT Application PCT/US2007/005643, filed Mar. 5, 2007, and published in English on Sep. 13, 2007, as International Publication No. WO 2007/103346, and which claims the benefit under 35 U.S.C. §119(e) of U.S. Provisional Patent Application Ser. No. 60/780,250, filed Mar. 8, 2006, the disclosure of each of which is incorporated herein by reference in its entirety.

This invention was made with government support under grant no. 0418499 from the National Science Foundation (Department of Materials Research). The US Government has certain rights to this invention.

FIELD OF THE INVENTION

This invention concerns degradable polyesters, methods of making and using the same, and articles such as biomedical implants formed therefrom.

BACKGROUND OF THE INVENTION

Biodegradable polyesters have significant potential for biomedical applications including tissue engineering, drug delivery, and biosensors. The most commonly used materials for these applications have been poly(L-lactic acid) (PLLA), poly(glycolic acid) (PGA), poly(ε-caprolactone) (PCL) and their copolymers (Wang, Y. et al., *Nat. Biotech.* 2002, 20, 602; Uhrich, K. E. et al., *Chem. Rev.* 1999, 99, 3181). However, many medical devices are implanted in dynamic environments of the body, which require elastomeric materials that will respond to these stresses. To minimize irritation of surrounding tissue, the material must be soft, resilient, and have similar mechanical properties. Furthermore, degradable materials are especially advantageous because they offer temporary mechanical support without the requirement of additional surgeries (Peppas, N. A.; Langer, R. *Science* 1994, 263, 1715).

The degradation kinetics of a material can be a strong function of the properties of the material, especially its morphology (Tm, Tg) and its topology (linear, branched, crosslinked). These parameters can affect the permeability of the material to reagents that can facilitate its degradation such as water and enzymes. Two general classes of these degradable polyester-based elastomers exist: thermoplastics and thermosets. While semicrystalline thermoplastics offer the advantage of ease of fabrication, they degrade heterogeneously due to the mixture of crystalline and amorphous regions. This can lead to rapid loss of mechanical properties as well as large deformation as the material degrades (Amsden, B. G. et al., *Biomacromolecules* 2004, 5, 2479). Conversely, amorphous thermosets offer more homogeneous degradation which leads to linear loss of mass and mechanical properties, as well as minimal deformation as the material degrades.

There are two general strategies toward preparing these amorphous thermoset elastomers. The first is to incorporate multifunctional monomers, such as glycerol or bis(ε-caprolactone-4-yl)propane (BCP), into the polymerization feed. Albertsson and Amsden have used both of these crosslinkers in ring opening polymerization (ROP) to form crosslinked PLLA and PCL containing materials (Palmgren, R. et al., *J. Poly. Sci., Part A: Poly. Chem.* 1997, 35, 1635; Palmgren, R. et al., *J. Poly. Sci., Part A; Poly. Chem.* 1997, 35, 1635; Amsden, B. G. et al., *Biomacromolecules* 2004, 5). Zhang, Tsutsumi, and Langer all provide examples of glycerol and sebacic acid based thermosets showing a wide range of mechanical and degradation properties (Nagata, M. et al., *J. Poly. Sci., Part A: Poly. Chem.* 1999, 37, 2005; Liu, Q. et al., *J. App. Poly. Sci.* 2005, 98, 2033). While the incorporation of multifunctional monomers provides a facile route to crosslinked materials, the resulting materials have very limited processing options.

The second approach to preparing these amorphous thermoset elastomers is to synthesize prepolymers containing reactive functional groups that can be subsequently crosslinked in a second step. This approach allows for the fabrication of materials using standard molding techniques, dramatically increasing the processing options of these materials. Amsden, Sepälä, and Storey all provide examples of crosslinking vinyl endgroup functionalized star-shaped PCL and PLLA prepolymers (Turunen, M. P. et al., *Polym. Int.* 2001, 51, 92; Storey, R. F. et al., *Polymer* 1997, 38, 6295). Nagata introduced aromatic cinnamic acid groups into the backbone of PCL to facilitate crosslinking in a second step (Nagata, M.; Sato, Y. *Polymer* 2003, 45, 87). Mikos has followed a similar strategy to prepare hydrogel materials (Jo, S. et al., *Macromolecules* 2001, 34, 2839). Fumaric acid was used to prepare unsaturated poly(ethylene glycol) PEG materials that were subsequently crosslinked using a radical initiator.

These examples of materials leave several issues to be addressed. First, the star-shaped materials all require added synthetic steps as the endgroups are functionalized postpolymerization. Second, nearly all of these prepolymers are semicrystalline, limiting their effectiveness as good candidates for preparing elastomeric materials. Third, the concentration of hydrolysable ester groups in the hydrogel materials is relatively low, limiting the degradability of these materials. Finally, none of these examples provide a facile option for tuning the hydrophilic or hydrophobic properties of these materials, which affects water uptake and degradation rates.

SUMMARY OF THE INVENTION

A first aspect of the present invention is a method of making an aliphatic polyester prepolymer, comprising: reacting, alone or in combination with other reactants, a diol with at least a first diacid (or a diester of said first diacid) to produce an aliphatic polyester prepolymer. The first diacid is preferably a trans-beta-hydromuconic acid (HMA; this term including derivatives such as diacid halides and diacid anhydrides therein). In some embodiments, the diol contains at least one ether linkage. In some embodiments the diol is further reacted with at a second diacid, or a diester of said second diacid, wherein said second diacid is different from said first diacid.

A second aspect of the present invention is an aliphatic polyester prepolymer containing an HMA residue and a diol residue (e.g., a diol containing at least one ether linkage). Such a prepolymer may be produced by a process as described above.

A third aspect of the present invention is a method of making an article (e.g., a stent or other biomedical implant), the article comprising a thermoset elastomeric polymer, with the method comprising: forming a prepolymer of as described above into said article, and then thermally crosslinking said prepolymer to produce said article.

A fourth aspect of the present invention is an article comprising a thermoset elastomeric polyester polymer produced containing an HMA residue and a diol residue, and article produced by a process as described above.

The foregoing and other objects and aspects of the present invention are explained in greater detail in the drawings herein and the specification set forth below.

DETAILED DESCRIPTION OF THE PREFERRED EMBODIMENTS

The present invention is explained in greater detail in the following discussion and examples, which are to be construed as illustrative and not limiting of the invention. The disclosures of all US patent references cited herein are to be incorporated by reference herein in their entirety.

Articles than can be made by the methods and materials of the invention include any types of article, including but not limited to biomedical implants, bandages, wound dressings and surgical aids, for which degradation is desired. Examples include but are not limited to bottles, containers, films, fibers (and including woven and nonwoven fabrics formed from such fibers), drug depots or drug delivery devices, stents (such as drug-eluting stents, as well as mechanical stents), ports, catheters, sheaths, sutures, scaffolds such as tissue engineering scaffolds, sheets, tubes, membranes, fasteners such as bone screws, leads, etc. The articles may consist entirely or consist essentially essentially of the polymers described herein, or may be composites formed with other materials such as fabrics, polymers including inert polymers, metals (gold, platinum, stainless steel), active agents (e.g., incorporated into drug eluting stents), combinations thereof, etc.

"Polyester" as used herein refers to a synthetic organic polymer, typically a condensation polymer, that contains an ester group in its main chain. Polyesters can be produced by the reaction of one or more diol monomers with one or more diacid or diester monomers. Hence the term "polyester" is inclusive of copolymers.

"Diol" as used herein refers to a compound, or mixture of compounds, having a pair of hydroxyl (—OH) groups. The diol may be a polyol. Examples of suitable diols include but are not limited to poly(ethylene glycol), poly(propylene glycol), poly(isopropylene glycol), polybutylene glycol), poly (1-methyl propylene glycol), poly(pentylene glycol), poly (diethylene glycol), poly(triethylene glycol), and combinations of two or more thereof. Diols used to carry out the present invention preferably include at least 1, 5, 10, 50, 100 or 200 or more ether linkages (—O—). Diols used in carrying out the present invention include aliphatic diols. The diols can be used alone or as combinations of different diols.

"Diacid" as used herein refers to a compound, or mixture of compounds, having a pair of carboxylic acid (—COOH) groups. Examples of diacids include but are not limited to adipic acid, glutaric acid, suberic acid, sebacic acid, dodecanedioic acid, isophthalic acid, terephthalic acid, azelaic acid, pimelic acid, 1,3-cyclohexane dicarboxylic acid, succinic acid, phthalic acid, isophthalic acid, trimellitic acid, maleic acid, fumaric acid, dimeric and trimeric fatty acids, dimethyl terephthalic and terephthalic acid-bis-glycol esters, etc. "Diacid" as used herein is also intended to cover corresponding derivatives, examples of which include but are not limited to diacid halides and diacid anhydrides. Particular examples of such diacid derivatives include but are not limited to phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid anhydride, adipoyl halide, sebacoyl halide, terephthaloyl halide, and the like. The diacid may include be an open chain aliphatic dicarboxylic acid, a cycloaliphatic dicarboxylic acid, an aromatic dicarboxylic acid, an open chain aliphatic dicarboxylic acid anhydride, a cycloaliphatic dicarboxylic acid anhydride, an aromatic dicarboxylic acid anhydride, an open chain dicarboxylic acid halide, a cycloaliphatic dicarboxylic acid halide, an aromatic dicarboxylic acid halide and mixtures thereof.

"Liquid" as used herein refers to an amorphous material that has a glass transition temperature or softening temperature below 25° C. or a semicrystalline material that melts below room temperature and has a glass transition temperature below 25° C.

A particularly preferred diacid for use herein is trans-β-hydromuconic acid (HMA) (including its derivatives such as its diacid halides and diacid anhydrides), alone or in combination with other diacids such as described above. HMA in underivitized form is represented by formula I:

(I)

"Diester of a diacid" as used herein refers to a diacid as described above in which the hydrogen of each hydroxyl group is replaced with another group "R", wherein the R groups may be the same or different. Any suitable group "R" may be used, including but not limited to alkyl, cycloalkyl, aryl, arylalkyl, heteroayl, etc., each of which may be linear or branched, saturated or unsaturated, and unsubstituted or substituted (e.g., 1, 2, 3 or more times) with an additional suitable substituent including but not limited to halo, nitro, cyano, hydroxyl, etc.

Diesters can be prepared by art-recognized techniques. For example they can be prepared by reacting the particular diacid with a sufficient amount of monoalcohol to react with both carboxylic acid groups. Specifically preferred diesters are divinyl adipate, bis(2,2,2-trichloroethyl) adipate, bis(2,2,2-trifluoroethyl) adipate, and diallyl adipate. See, e.g., U.S. Pat. No. 5,478,910.

"Polymerization initiator" as used herein may be any suitable initiator, examples of which include but are not limited to 2,2'-azobisisobutyronitrile (AIBN), acetylperoxide, laurylperoxide, tert-butyl peracetate, tert-butyl hydroperoxide and di-tert-butylperoxide. See, e.g., U.S. Pat. No. 6,818,376; see also U.S. Pat. Nos. 6,811,960 and 6,410,652.

"Crosslinking agent" as used herein may be any suitable crosslinking agent, including but not limited to unsaturated and polyunsaturated crosslinking agents, and crosslinking agents containing acrylic, methacrylic, and vinylic unsaturation. Examples of suitable crosslinking agents include but are not limited to N-vinylpyrrilidone (NVP), methyl methacrylate, methyl acrylate, acrylonitrile, acrylic acid, vinyl acetate, PEG triacrylate, PEG diacrylate, styrene, butadiene derivatives, etc. See, e.g., U.S. Pat. Nos. 6,881,786 and 6,352,667.

"Active agent" as used herein broadly refers to an agent or substance including, but not limited to, a therapeutic substance, a polymer impregnated with therapeutic substance, radioactive isotope, and radiopaque material, that possesses desirable therapeutic or diagnostic characteristics. The agent may be, for example, antineoplastic, antimitotic, antiinflammatory, antiplatelet, anticoagulant, antifibrin, antithrombin, antiproliferative, antibiotic, antioxidant, antiallergic substances, or cell cycle inhibitors (e.g., sirolimus), as well as combinations thereof. Examples of such antineoplastics and/or antimitotics include paclitaxel, docetaxel, methotrexate, azathioprine, actinomycin-D, vincristine, vinblastine, fluorouracil, doxorubicin hydrochloride, and mitomycin. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril, cilazapril or lisinopril; calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include alpha-interferon, Trapidil antiplatelet (manufactured by DAITO Corporation, Japan), genetically engineered epithelial cells, and dexamethasone. In yet other embodiments, the active substance is a radioactive isotope or radioopaque compound used in nuclear medicine procedures. Examples of radioactive isotopes include, but are not limited to, phosphoric acid ($H_3P^{32}O_4$), palladium ($Pd^{103}$), cesium ($C^{311}$), and iodine ($I^{125}$). See, e.g., U.S. Pat. No. 6,765,505; see also U.S. Pat. Nos. 6,918,929 and 6,805,898.

Polyester prepolymer compounds of the invention can be produced by any suitable technique such as by condensation of a diol with a diacid (optionally with removal of water so produced, such as by azeotrope distillation), alcoholic trans-esterification (where a diester of a diacid is utilized, hence forming an alcohol rather than water as a reaction product), acylation (where a diacid in the form of an acid halide, such as an acid chloride is used), the silyl method (where carboxylic acid chloride is converted with a trimethyl silyl ether of an alcohol component and trimethyl silyl chloride is produced), the acetate method, etc. Ring-opening polymerizations are less preferred for carrying out the method of the invention.

Catalysts that may be used include salts of Li, Ca, Mg, Mn, Zn, Pb, Sb, Sn, Ge, and Ti, such as acetate salts and oxides, including glycol adducts, and Ti alkoxides. These are generally known in the art, and the specific catalyst or combination or sequence of catalysts used may be readily selected by a skilled practitioner. The preferred catalyst and preferred conditions differ depending on whether the diacid monomer is polymerized as the free diacid or as a diester. See, e.g., U.S. Pat. No. 5,959,066.

Enzyme catalysts useful for making polyesters, and which can be used in the present invention, are also well known. Examples include but are not limited to *Candida* Cylindracea Lipase L-1754, Subtilisin Carlesberg Protease P-5380 (E.C. no. 3.4.4.16), and PPL (L-3082 and L-3126) (available from Sigma Chemical Company), and the various Lipozyme products, Novozyme No435, SP-523, SP-525, and SP-526 (available from Novo Nordisk). See, e.g., U.S. Pat. No. 5,478,910.

The reaction conditions for making the polyester prepolymer are not critical. Any suitable time and temperature may be employed, such as a temperature of 0° C. to 100° C. for a time of 1 minute to 10 hours or more. The reaction may be carried out in a suitable organic or inorganic solvent, under aqueous or nonaqueous conditions, and may be carried out in the liquid, gas, or supercritical fluid phase. See, e.g., U.S. Pat. No. 5,478,910. The prepolymer compounds may be produced at any suitable weight, e.g., from 500 or 1,000 grams per mole to 20,000 or 50,000 grams per mole, or more.

The polyester prepolymer compositions produced by the reaction are in general liquid and/or amorphous at a temperature of 25° C. The prepolymers can be used immediately or packaged and stored for subsequent use or sale.

The prepolymer compositions may optionally be combined with or blended with one or more additional ingredients, each of which may be included in any suitable amount. Examples of such additional ingredients include but are not limited to polymerization initiators (e.g., from 0.001 to 1 or 2 percent by weight, or more), crosslinking agents (e.g., from 0.1 or 0.5 to 5 or 10 percent by weight, or more), active agents (e.g., from 0.001 or 0.01 to 1, 5 or 10 percent by weight, or more), fillers (e.g., from 1 or 5 to 20 or 50 percent by weight, or more), etc., and combinations thereof. In some embodiments these additional ingredients may be kept separate from the prepolymer and deposited, blended or formed concurrently with the prepolymer into the article, as discussed further below.

Polyester prepolymers as described above can be formed into useful articles by any suitable technique such as molding, spraying, dip coating, free meniscus coating, etc., depending upon the particular article being produced. The prepolymers can be combined with other constituents (such as active agents, pigments, inorganic fillers, or proteins), depending on the particular article being formed. The prepolymers can be applied to or combined with another material, including inert materials that serve as a "core" for the prepolymer in the finished article (e.g., a metallic mesh, lattice or the like for a stent or drug eluting stent). Once applied or formed, the prepolymer can be thermoset by heating in accordance with known techniques (e.g., by heating to a temperature of 100 to 160° C. or more, for a time of 10 minutes to 48 hours). Depending upon the intended use of the article (e.g., as a biomedical implant or surgical aid), the article may be optionally sterilized and aseptically packaged for subsequent use. The thermoset polyester portion of the article (that is, apart from any inert or non-degradable core, lattice, or the like, may comprise or consist essentially of from 0.001 or 0.01 to 1, 5 or 10 percent by weight of an active agent as described above).

In some embodiments, articles or materials of the invention completely degrade (i.e., no residual polymer) in six months. By "complete degradation" or "completely degrades" is meant complete mass loss of the polymer of the invention from the article or material when it is immersed in phosphate buffered saline solution (0.01M at pH 7.4) at 37° C. When the article is a composite of a degradable polymer as described herein and a stable component such as an inert polymer, metal, inorganic material, or composite thereof, then "complete loss" refers to loss of the polymer of the invention only and not to the inert portion of the composite article.

In some embodiments, articles or materials of the invention have a Young's modulus of not less than 0.02 MPa. "Youngs Modulus" is defined as the slope of the low strain (from 0 to 1.0% elongation) region of the stress v. strain plot obtained from mechanical testing on an Instron instrument with a crosshead speed of 20 mm/min "Youngs Modulus" is more generally defined as the resistance to deformation of the material.

The present invention is explained in greater detail in the following non-limiting Examples.

Example 1

Our laboratory has previously reported the preparation of linear, unsaturated polyesters through the condensation polymerization of trans-β-hydromuconic acid (HMA) and various aliphatic diols. Several classes of materials were prepared that demonstrated a wide range of thermal and solubility properties. Among these various classes of materials were amorphous poly(ester ether) materials prepared by using diethylene glycol as the diol. We will describe the synthesis of an expanded series of these materials by using ethylene glycol (EG) dimers, trimers, and tetramers as the diols. This method eliminates the need for additional postpolymerization functionalization reactions and provides good candidates for elastomers since these prepolymers are amorphous. These prepolymers were subsequently thermally crosslinked with a free radical initiator to form amorphous elastomeric materials. The ability to tune the water uptake, crosslinking density, thermal, and mechanical properties of these materials will be demonstrated.

Experimental

Materials. All materials were purchased from Aldrich and used as received unless otherwise noted. EG oligomers were all ≧99.5% pure. HMA was recrystallized from water and acetonitrile prior to use, Novozyme-435 was dried under vacuum at 25° C. for 24 h prior to use.

Characterization. $^1$H and $^{13}$C NMR spectra were acquired in deuterated chloroform on a Bruker 400 AVANCE or Bruker 300 AMX spectrometer. Molecular weights, relative to narrow polystyrene standards, were measured using a Waters GPC system with a Wyatt Optilab DSP interferometric refractometer and a Wyatt Dawn EOS as the detectors. The measurements were taken at 40° C. with tetrahydrofuran as the mobile phase on three columns (Waters Styragel HR2, HR4, HR5). Glass transitions and melting points were measured with a Seiko 220C differential scanning calorimeter, using a heating and cooling rate of 10° C./min. Thermogravimetric analysis was carried out using a Perkin Pyris 1 TGA with a heating rate of 10° C./min in a $N_2$ atmosphere, Elemental analysis was performed by Atlantic Microlab, Inc. Glass transitions were determined at the inflection point of the endotherm and melting and crystallization points were determined at the peak of the endotherm or exotherm respectively.

Polymerization. Enzyme Catalysis. A 10 mL round bottom flask was charged with equimolar amounts of HMA and diol and flushed with an argon atmosphere. The mixture was stirred at 115° C. using magnetic stirring, until a homogeneous melt was formed. The melt was cooled to 90° C. and Novozyme-435 (10% by total monomer weight) was added. The heterogeneous mixture was stirred for 6 h and then the pressure was reduced to 300 mmHg. After 24 h of total reaction time, the pressure was further reduced to 40 mmHg and the viscous mixture was allowed to stir for an additional 24 h. The catalyst was removed by filtration after diluting the mixture with chloroform (2 mL). Following catalyst removal, chloroform was removed under vacuum. Reactions were preformed on a 5 g scale.

Metal Catalysis, A 10 mL round bottom flask was charged with equimolar amounts of HMA and diol and flushed with an argon atmosphere. The mixture was stirred at 130° C. using magnetic stirring, until a homogeneous melt was formed. Next, $Sn(Oct)_2$ (1.0 mol %) was added to the melt. The mixture was stirred for 1 h and then the pressure was reduced to 20 mmHg. The reaction was allowed to proceed at 20 mmHg for 23 h, for a total reaction time of 24 h. Polymerization was terminated by precipitating the polymer into cold methanol. All reactions were preformed on a 5 g scale.

Poly(diethylene glycol hydromuconoate). $^1$H NMR: δ (ppm)=5.65 (m, 2H), 4.19 (t, 4H, J=4.6 Hz), 3.67 (t, 4H, J=3.5 Hz), 3.07 (dd, 4H, J=1.6, 3.7 Hz), $^{13}$C NMR δ (ppm)=171.35 ($CO_2$), 125.72 (—CH═$CHCH_2$—), 68.78 (—$CO_2CH_2CH_2O$—); 63.53 (—$CO_2CH_2CH_2O$—), 37.43 (—$CH_2CH$═CH—). Anal. Calcd for $C_{10}H_{14}O_5$: C, 56.07; H, 6.59; O, 37.34. Found: C, 55.98 H, 6.66. Yield 96% ($Sn(Oct)_2$), 88% (Enzyme).

Poly(triethylene glycol hydromuconoate). $^1$H NMR: δ (ppm)=5.65 (m, 2H), 4.19 (t, 4H, J=4.7 Hz), 3.67 (t, 4H, J=5.0 Hz), 3.61 (s, 4H), 3.07 (dd, 4H, J=1.5, 3.7 Hz), $^{13}$C NMR δ (ppm)=171.45 ($CO_2$), 125.82 (—CH═$CHCH_2$—), 70.45 (—$CO_2CH_2CH_2O$—), 69.00 (—$OCH_2CH_2O$—), 63.69 (—$CO_2CH_2CH_2O$—), 37.56 (—$CH_2CH$═CH—). Anal. Calcd for $C_{12}H_{18}O_6$: C, 55.81; H, 7.02; O, 37.17. Found: C, 55.99 H, 6.86. Yield 93%.

Poly(tetraethylene glycol hydromuconoate). $^1$H NMR: δ (ppm)=5.64 (m, 2H), 4.18 (t, 4H, J=4.7 Hz), 3.65 (t, 4H, J=4.9 Hz), 3.60 (s, 8H), 3.07 (dd, 2H, J=1.5, 3.8 Hz). $^{13}$C NMR δ (ppm)=171.41 ($CO_2$), 125.81 (—CH═$CHCH_2$—), 70.50 (—$CO_2CH_2CH_2O$—), 68.95 (—$OCH_2CH_2O$—), 63.70 (—$CO_2CH_2CH_2O$—), 37.54 (—$CH_2CH$═CH—). Anal. Calcd for $C_{14}H_{23}O_7$: C, 55.43; H, 7.64; O, 36.92. Found: C, 55.31 H, 7.66. Yield 96%.

Poly(diethylene glycol hydromuconoate-co-diethylene glycol adipate). $^1$H NMR: δ (ppm)=5.66 (m, 2H), 4.19 (t, 4H, J=4.8 Hz), 3.65 (t, 4H, J=4.8 Hz), 3.10 (dd, 4H, J=1.7, 3.8 Hz), 2.33 (t, 4H, J=7.0 Hz), 1.63 (m, 4H). $^{13}$C NMR: δ (ppm)=173.44 ($CO_2$, AA), 171.66 ($CO_2$, HMA), 125.88 (—CH═$CHCH_2$—), 64.77 (—$CH_2O$, HMA:OD), 64.41 (—$CH_2O$, AA:OD), 37.79 (—$CH_2CO_2$, HMADD), 33.86 (—$CH_2CO_2$, AA:OD), 29.02 (—$CH_2CH_2CH_2O$), 28.50 (—$CH_2CH_2O$, HMA:OD), 28.44 (—$CH_2CH_2O$, AA:OD), 25.75 (—$CH_2CH_2O$, HMA:OD), 25.71 (—$CH_2CH_2O$, AA:OD), 24.34 (—$CH_2CH_2CO_2$, AA). $^1$H NMR varies only by the relative integrated peak areas for all copolymers. $^{13}$C NMR are identical for all copolymers.

Elemental analysis is listed by mol percent HMA in the copolymer. Anal. Calcd 10% HMA: C, 55.39; H, 7.72; O, 36.89. Found: C, 55.28 H, 7.60, Anal. Calcd 20% HMA: C, 55.50; H, 7.54; O, 36.96. Found: C, 55.61 H, 7.66. Anal. Calcd 30% HMA: C, 55.60; H, 7.37; O, 37.03. Found: C, 55.68 H, 7.45. Anal. Calcd 40% HMA: C, 55.71; H, 7.19; O, 37.10. Found: C, 55.80 H, 7.26. Yields are listed by the diol used to prepare the given polymer. 10% HMA: 98% yield. 20% HMA: 95% yield. 30% HMA: 97% yield. 40% HMA: 95% yield.

Crosslinking. Elastomer slabs were prepared by spreading a mixture of the liquid prepolymer (0.25 g), appropriate amount of NVP (0-16.0 wt. %), and appropriate amount of radical initiator (0.5-10.0 wt. %) on a glass mold (50 mm×15 mm). The mixture was heated in an oven for the prescribed time, at the prescribed temperature, after which the slab was removed. Following removal, the slab was allowed to cool to room temperature and was removed from the mold with a razor.

Network and Swelling. Sol-Gel analysis was conducted by swelling a 0.15 g elastomer slab in methylene chloride for 24 h at 25° C. The solvent was removed and the percent soluble fraction ($Q_s$) was determined according to the following equation $$Q_s = \left(\frac{m_i - m_f}{m_i}\right) \times 100$$

where $m_i$ and $m_f$ represent the initial and final mass. Each measurement was preformed on three separate samples. The value was reported as the average of the three measurements. All error bars represent a 95% confidence interval.

Mechanical Analysis. Mechanical data were collected on an Instron 5566 at a crosshead speed of 20 mm/min at 25° C. The Young's modulus (G) was calculated using the initial linear portion of the stress/strain curve (1-5% strain). The crosslinking density v was calculated according to the following equation $$v = \frac{G}{3RT}$$

where R represents the universal gas constant and T is the temperature in K. Each measurement was preformed on three separate samples. The value was reported as the average of the three measurements.

Degradation. Slabs of elastomer (0.15 g) were placed in 0.01 M pH 7.4 phosphate buffer saline solutions at 37° C. At the prescribed intervals, the slab was removed from the buffer solution. The Young's modulus was measured on the wet slab using the same conditions as above. Following mechanical testing, the slab was dried under vacuum for 24 h and the mass was measured. Each measurement was performed on three separate samples. All error bars represent a 95% confidence interval. Mass loss (ML) was calculated according to the following equation:

$$ML = \frac{m_i - m_t}{m_i} \times 100$$

where $m_i$ and $m_t$ represent the initial mass and mass at time t. Kinetics of degradation and loss of mechanical properties were calculated according to first order kinetics. A plot of ln(loss) v. t was fitted with a linear regression.

Water Uptake. Slabs of elastomer (0.15 g) were placed in 0.01 M pH 7.4 phosphate buffer saline solutions at 37° C. At the prescribed intervals, the swollen network was removed from the buffer solution, blotted dry, and the mass was recorded. Each measurement was preformed on three separate samples. The water uptake (WU) was calculated according to the following equation:

$$WU = \frac{m_s - m_d}{m_d} \times 100$$

where $m_s$ and $m_d$ represent the swollen and dry mass, respectively. The value was reported as the average of the three measurements. All error bars represent a 95% confidence interval.

Cytotoxicity Testing. STS Duotek (Rush, N.Y.) performed all cytotoxicity analysis, Minimum Essential Medium (MEM) elution tests were performed according to the ISO 10993-5 standard. Samples were extracted for 24 h at 37° C. and pH=7.4 in minimal essential medium. Extracts were placed on cell monolayers for 48 h at 37° C. and pH=7.4. L929 mouse fibroblast cells from the ATCC cell line were used. At the conclusion of 48 h, the cells were examined and cytotoxicity was scored on a 0 to 4 scale, 0 being the least cytotoxic.

Results and Discussion

Previous investigations in our laboratory discovered a class of amorphous poly(ester ether) materials prepared from the condensation polymerization of HMA and diethylene glycol. The amorphous nature and ability to crosslink these materials makes them good candidates for preparing elastomeric materials. The desire for elastomers with tunable mechanical and degradation properties has lead us to prepare a series of these poly(ester ether) prepolymers from the condensation polymerization of HMA and ethylene glycol dimers (2EG), trimers (3EG), and tetramers (4EG). Prepolymers with number-average molecular weights near $5.0 \times 10^3$ were prepared, with molecular weights slightly increasing as the length of the EG oligomer increased (Scheme 1, Table 1). Novozyme-435, consisting of lipase B from *Candida antarctica* immobilized on a Lewatit macroporous resin, and $Sn(Oct)_2$ were both used as catalysts. Glass transition temperatures were all below −30° C. with the EG oligomer length not having much of an effect.

Scheme 1. Synthesis of unsaturated poly(ester-ether) prepolymers

-continued

TABLE 1

Characterization of poly(ester-ether) prepolymers

| prepolymer | EG diol | $<M_n> \times 10^{-3}$ (g/mol)$^a$ | PDI$^a$ | $T_g$ (° C.)$^b$ | weight loss (° C.)$^c$ 5% | 10% |
|---|---|---|---|---|---|---|
| 1 | 2$^d$ | 4.9 | 1.7 | −33 | 302 | 326 |
| 2 | 2$^e$ | 6.4 | 1.2 | −32 | 298 | 319 |
| 3 | 3$^d$ | 4.9 | 1.9 | −33 | 274 | 316 |
| 4 | 4$^d$ | 5.6 | 1.8 | −36 | 301 | 319 |

Figure 1:
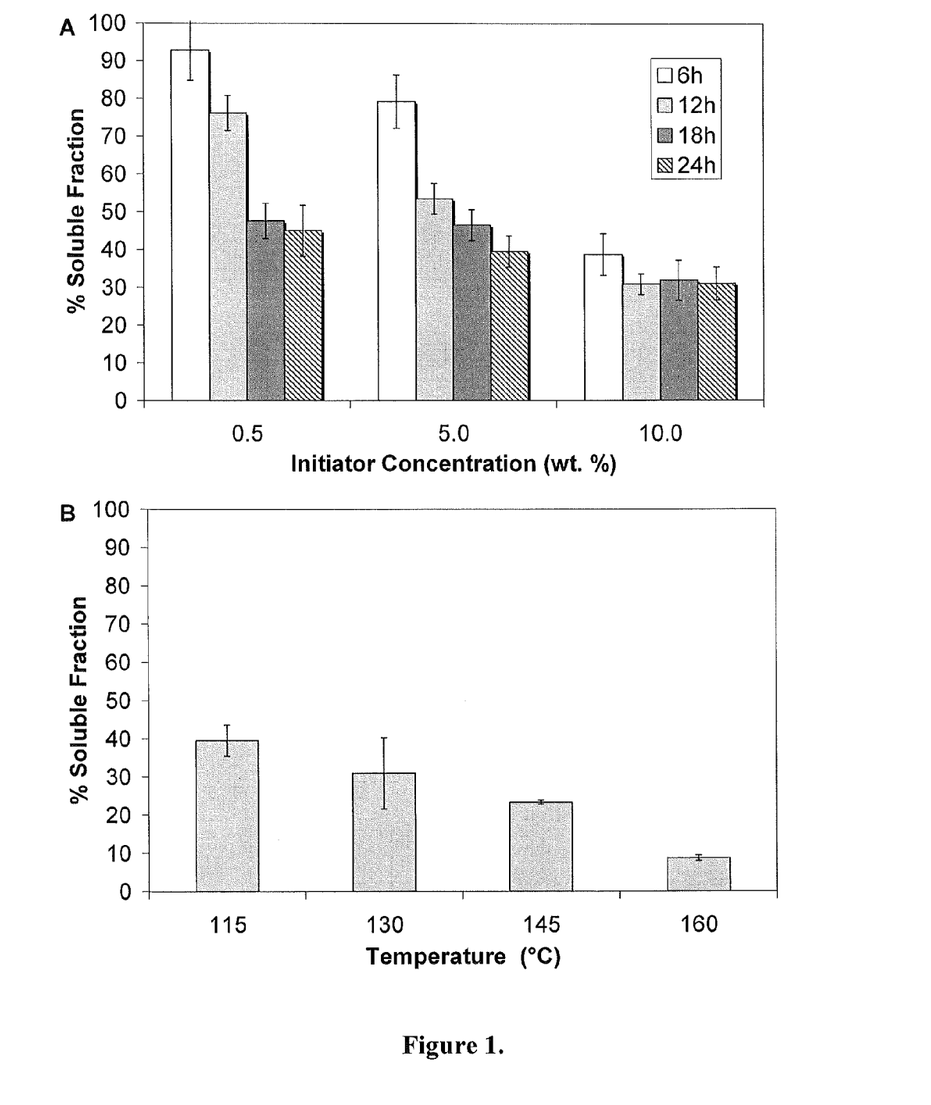
FIG. 1. The effect of a) BPO concentration and curing time, and b) curing temperature on the soluble fraction of the elastomer materials.

$^a$Determined by GPC
$^b$Determined by DSC, second heat, 10° C./min
$^c$Determined by TGA in N$_2$, 10° C./min
$^d$1.0 mol % Sn(Oct)$_2$ catalyst, 48 h
$^e$10.0 wt. % Novozyme-435 catalyst, 24 h Having successfully prepared unsaturated prepolymers, crosslinking conditions of these materials were explored. Initially, benzoyl peroxide (BPO) was used as the free radical initiator. Details of later experiments that used other free radical initiators will be described below. Initiator concentration, curing time, and curing temperature were all varied to investigate the effect that each had on the sol fraction (Q$_s$) of the resulting material (FIG. 1). All of these studies were performed on Prepolymer 1. Soluble fractions decreased as the initiator concentration increased from 0.5 to 10.0 wt. percent at a curing temperature of 115° C. Similarly, they decreased as the curing time increased from 6 to 24 h, again at a curing temperature of 115° C. Although at 24 h, materials demonstrate similar soluble fractions regardless of initiator concentration. Finally, the curing temperature was varied from 115 to 160° C. using 5.0 wt. % BPO and a curing time of 24 h in all cases. Soluble fractions again noticeably decreased as the curing temperature increased.

Based on the above results, curing conditions of 5.0 wt. % BPO, 130° C. for 24 h were used for all subsequent investigations. The thermal and mechanical properties of elastomers prepared from HMA:nEG prepolymers using these curing conditions were investigated. Crosslinking raised the glass transition temperatures of the materials to between −10 and −20° C., with materials prepared from 4EG demonstrating the lowest transition temperature (Table 2). Crosslinking densities steadily decreased as the EG length increased resulting from a lower concentration of double bonds in the backbone of the material. The swelling indices follow a similar trend. Correspondingly, the Young's modulus (G) and ultimate stress (ε) of the materials decreased as the EG length increased, while the ultimate extension (σ) increased.

TABLE 2

Effect of ethylene glycol oligomer length and BPO concentration on thermal and mechanical properties of elastomers cured at 130° C. for 24 h

| elastomer | EG | $T_g$ (° C.)$^a$ | G (MPa)$^b$ | ε (MPa)$^b$ | σ (%)$^b$ | ν (mmol/L)$^b$ |
|---|---|---|---|---|---|---|
| 1 | 2$^c$ | −13 | 0.32 | 0.21 | 122 | 43.1 |
| 2 | 2$^d$ | −13 | 0.47 | 0.42 | 89 | 63.2 |
| 3 | 2$^e$ | −11 | 0.37 | 0.36 | 92 | 49.8 |
| 4 | 3$^e$ | −21 | 0.27 | 0.15 | 98 | 36.3 |
| 5 | 4$^e$ | −22 | 0.16 | 0.11 | 127 | 20.9 |

$^a$Determined by DSC, second heat, 10° C./min
$^b$Determined by Instron, 20 mm/min crosshead speed
$^c$0.5 wt. % BPO
$^d$10.0 wt. % BPO
$^e$5.0 wt. % BPO Having successfully prepared elastomeric materials, efforts were undertaken to prepare materials that demonstrated a wider range of mechanical and thermal properties. Three efforts toward this goal were undertaken. First, copolymerric prepolymers where the amount of HMA was diluted out by a second saturated diacid, adipic acid (AA), were prepared. Second, different free radical initiators were investigated. Third, N-vinyl pyrrolidone was used as a crosslinking agent in an attempt to increase crosslinking densities.

First, the copolymer approach was investigated (Scheme 2). By diluting out the amount of HMA in the material with AA, the amount of crosslinkable groups in the material would subsequently be reduced. This would allow for control over the crosslinking densities of the subsequent crosslinked elastomer materials. Diethylene glycol was used as the diol for all of these investigations. Materials with number-average molecular weights near 4.0×10$^3$ were prepared (Table 3). Observed monomer incorporation was identical to the ratio of monomers in the polymerization feed. Copolymers demonstrated a window of glass transition temperatures ranging from −45 to −30° C. Yields were above 96% for all materials.

Scheme 2. Synthesis of unsaturated poly(ester ether) copolymers

Figure 2:
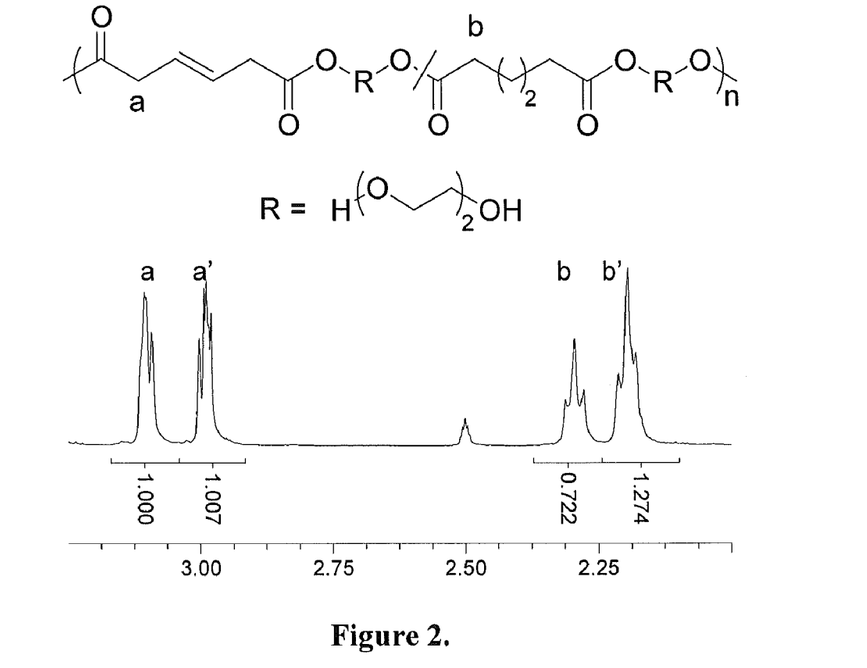
FIG. 2. $^1$H NMR peaks of HMA:AA copolymer used to determine monomer incorporation, after 1 h of reaction time (Prime (') sign denotes monomer proton).
Figure 3:
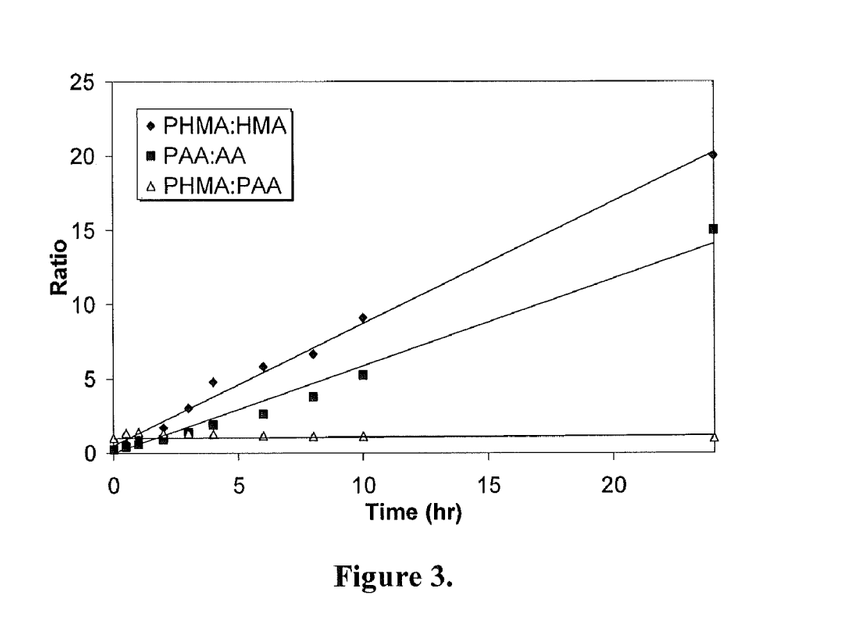
FIG. 3. Characterization of monomer incorporation into HMA:AA copolymers as determined by $^1$H NMR where PHMA and PAA are the amount of the respective monomers that have been incorporated into the copolymer.

Clearly, the manor of the distribution of the two diacid monomers (random or segmented) will have an effect on the network structure and hence the mechanical properties of the elastomer materials. As a result, the distribution of these two monomers was investigated. This was investigated by monitoring a copolymerization reaction where the molar ratio of the two diacid monomers (0.5:0.5:1) was equal. The incorporation of the two monomers was monitored by $^1$H NMR during polymerization (FIG. 2). Subsequently, the relative ratios of the respective polymer to monomer peak integrals were plotted versus time (FIG. 3). This plot shows that while HMA is being incorporated into the copolymer slightly faster (k=0.82) than adipic acid (k=0.59), the relative rates are fairly similar. Furthermore, when the relative ratios of the two polymer peak integrals are plotted versus time, the ratio is nearly constant at 1, supporting the conclusion that these materials are random copolymers.

TABLE 3

Characterization of HMA:AA copolymers

| prepolymer | HMA:AA:DEG ratio targeted | HMA:AA:DEG ratio observed[a] | $<M_n> \times 10^{-3}$ (g/mol)[b] | PDI[b] | $T_g$ (° C.)[c] | weight loss (° C.)[d] 5% | 10% |
|---|---|---|---|---|---|---|---|
| 5 | 0:50:50 | 0:50:50 | 3.3 | 1.9 | −46 | 268 | 290 |
| 6 | 10:40:50 | 10:40:50 | 4.3 | 1.7 | −44 | 322 | 340 |
| 7 | 20:30:50 | 20:30:50 | 3.9 | 1.7 | −40 | 314 | 337 |
| 8 | 30:20:50 | 30:20:50 | 4.1 | 1.7 | −37 | 298 | 326 |
| 9 | 40:10:50 | 40:10:50 | 4.0 | 1.7 | −33 | 300 | 318 |
| 10 | 50:0:50 | 10:40:50 | 4.9 | 1.7 | −31 | 302 | 326 |

[a]Determined by $^1$H NMR
[b]Determined by GPC
[c]Determined by DSC, second heat, 10° C./min
[d]Determined by TGA in $N_2$, 10° C./min The thermal properties of Prepolymers 5-10 were also used to investigate the nature of the incorporation of HMA and AA. The glass transition temperature is a useful piece of data for this investigation for two reasons. First, if a material were segmented in nature, one would expect the possibility of the material displaying two glass transition temperatures. All of the copolymers prepared display a single, clear glass transition temperature (Table 3). Second, a derivative of the Fox equation for random copolymers can be applied to this series of copolymers, where $w_1$ and $w_2$ are the respective fractions of the two monomers, and $T_{g1}$ and $T_{g2}$ are the glass transition temperatures of the homopolymers prepared from the respective monomers.

$$T_g = w_1 T_{g1} + w_2 T_{g2}$$

Figure 4:
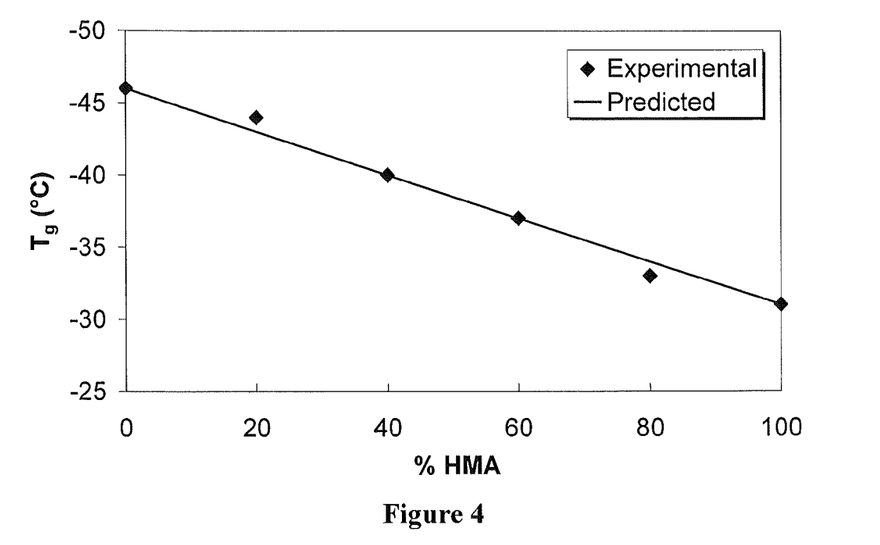
FIG. 4. Glass transition temperature of HMA:AA copolymers determined experimentally and predicted theoretically by the Fox equation.

The plot of the transition temperatures predicted by the Fox equation is in very close agreement with the transition temperature measured experimentally (FIG. 4), further supporting that the copolymers prepared are random in nature.

Following the preparation of copolymer materials, they were crosslinked using similar curing conditions of 5.0 wt. % BPO for 24 h at 130° C. Indeed, the mechanical and thermal properties of the resulting elastomers correlated well with the amount of HMA in the material (Table 4 and 5). Glass transition temperatures increased from −40 to −10° C. as the amount of HMA in the material increased. Furthermore, the Young's modulus and ultimate stress steadily increased as the amount of HMA in the material increased, while the ultimate elongation decreased. Materials with ultimate elongation over 170% were prepared. Correspondingly, the crosslinking density and the swelling index increased as the amount of HMA in the material increased.

TABLE 4

The effect of the amount of HMA in the elastomer material on the thermal properties of materials cured at 130° C. for 24 h with 5.0 wt. % BPO

| elastomer | HMA:AA ratio[a] | $T_g$ (° C.)[b] | Weight Loss (° C.)[c] 5% | 10% |
|---|---|---|---|---|
| 6 | 20:80 | −39 | 296 | 320 |
| 7 | 40:60 | −34 | 299 | 325 |
| 8 | 60:40 | −25 | 287 | 313 |

TABLE 4-continued

The effect of the amount of HMA in the elastomer material on the thermal properties of materials cured at 130° C. for 24 h with 5.0 wt. % BPO

| elastomer | HMA:AA ratio[a] | $T_g$ (° C.)[b] | Weight Loss (° C.)[c] 5% | 10% |
|---|---|---|---|---|
| 9 | 80:20 | −14 | 285 | 307 |
| 10 | 100:0 | −11 | 275 | 299 |

[a]Molar ratio
[b]Determined by DSC, second heat, 10° C./min
[c]Determined by TGA in $N_2$, 10° C./min.

TABLE 5

The effect of the amount of HMA in the elastomer on the mechanical and network properties of the materials cured at 130° C. for 24 h with 5.0 wt. % BPO

| elastomer | G (MPa)[a] | ε (MPa)[a] | σ (%)[a] | ν (mmol/L)[a] |
|---|---|---|---|---|
| 6 | 0.10 | 0.07 | 153 | 13.5 |
| 7 | 0.13 | 0.10 | 172 | 17.5 |
| 8 | 0.19 | 0.15 | 112 | 25.6 |
| 9 | 0.24 | 0.17 | 95 | 32.3 |
| 10 | 0.37 | 0.36 | 92 | 49.8 |

[a]Determined by Instron, 20 mm/min crosshead speed

Having investigated the use of copolymeric prepolymers to modify the mechanical and thermal properties of the elastomeric materials, the effect of the radical initiator was investigated. A second commonly used radical initiator, 2,2'-Azobis(2-methylpropionitrile) (AIBN), was used to cure HMA: 2EG prepolymers at 130° C. using initiator concentrations between 0.5 and 10.0 wt. %. The use of AIBN clearly affected the properties of the materials compared to BPO (Table 6 and 7).

TABLE 6

Effect of AIBN initiator on thermal properties of elastomers prepared from HMA:2EG prepolymers at 130° C. for 24 h

| | Wt. % | | weight loss (° C.)[b] | |
|---|---|---|---|---|
| elastomer | AIBN | $T_g$ (° C.)[a] | 5% | 10% |
| 11 | 0.5 | 4 | 266 | 290 |
| 12 | 5.0 | −1 | 262 | 285 |
| 13 | 10.0 | −2 | 265 | 289 |

[a]Determined by DSC, second heat, 10° C./min
[b]Determined by TGA in $N_2$, 10° C./min

TABLE 7

Effect of AIBN initiator on mechanical properties of elastomers prepared from HMA:2EG prepolymers at 130° C. for 24 h

| elastomer | wt. % AIBN | G (MPa)[a] | ε (MPa)[a] | σ (%)[a] | ν (mmol/L)[a] | Q (%)[b] |
|---|---|---|---|---|---|---|
| 11 | 0.5 | 1.5 | 0.7 | 65 | 202 | 16 |
| 12 | 5.0 | 1.6 | 0.8 | 63 | 215 | 18 |
| 13 | 10.0 | 2.0 | 0.7 | 75 | 269 | 15 |

[a]Determined by Instron, 20 mm/min crosshead speed
[b]Extracted in methylene chloride for 24 h at 25° C.

The glass transition temperatures of the elastomers increased from nearly −15° C. to approximately 0° C. Mechanically, the Young's modulus more than doubled, ranging from 1.5 to 2.0 MPa. Accordingly, crosslinking densities increased by approximately 5 times and soluble fractions decreased by approximately 10%.

Finally, the effect of adding NVP to the mixture of initiator and prepolymer was investigated. NVP was chosen because it is a reactive vinyl monomer that has precedence in the literature for being used to promote crosslinking. It is has also been shown to reduce surface protein absorption because of its hydrophilicity. AIBN was used as the initiator for all of these studies. Crosslinking conditions were 5.0 wt. % of initiator at 130° C. for 24 h with varying amount of NVP added to the mixture. The addition of NVP did not have a large effect on the thermal properties of the resulting materials (Table 8). Glass transition temperatures were similar to those from materials crosslinked with AIBN without the addition of any NVP, with the $T_g$'s actually going down as the amount of NVP increased. This decrease is a result of short dimer and trimer chains of NVP forming during the crosslinking process, which reduces the $T_g$ of the material because barriers to rotation are reduced. As the amount of NVP increases, so does the probability of the formation of these dimer and trimer chains. However, even with this reduction, glass transitions temperatures were still always greater than crosslinked materials that used BPO as the radical initiator.

TABLE 8

Effect of NVP on thermal properties of elastomers using 5.0 wt. % AIBN at 130° C. for 24 h

| | wt. % | | | weight loss (° C.)[b] | |
|---|---|---|---|---|---|
| elastomer | EG | NVP | $T_g$ (° C.)[a] | 5% | 10% |
| 12 | 2 | 0.0 | −1 | 262 | 285 |
| 14 | 2 | 1.0 | 2 | 275 | 297 |

TABLE 8-continued

Effect of NVP on thermal properties of elastomers using 5.0 wt. % AIBN at 130° C. for 24 h

| | wt. % | | | weight loss (° C.)[b] | |
|---|---|---|---|---|---|
| elastomer | EG | NVP | $T_g$ (° C.)[a] | 5% | 10% |
| 15 | 2 | 2.0 | 3 | 271 | 295 |
| 16 | 2 | 4.0 | −10 | 262 | 288 |
| 17 | 2 | 8.0 | −13 | 265 | 291 |
| 18 | 2 | 16.0 | −13 | 273 | 299 |
| 19 | 4 | 0.0 | −17 | 274 | 297 |
| 20 | 4 | 1.0 | −22 | 273 | 296 |
| 21 | 4 | 4.0 | −26 | 268 | 293 |
| 22 | 4 | 16.0 | −27 | 265 | 289 |

[a]Determined by DSC, second heat, 10° C./min
[b]Determined by TGA in $N_2$, 10° C./min While the addition of NVP did not have a large effect on the thermal properties of the resulting materials, the mechanical properties were dramatically improved (Table 9). Materials with a Young's modulus as high as 20 MPa were prepared. Correspondingly, the ultimate stress values and crosslinking densities also increased. However, there is a maximum at 4.0 wt. % NVP that is reached with these improvements in mechanical properties. Control experiments were run to investigate the origin of this maximum. NVP was crosslinked with 5.0 wt. % AIBN at 130° C. for 24 h without the addition of any prepolymer. The resulting material was extremely brittle, so much so that it was impossible to perform mechanical testing of the material. Clearly, there is a balance between having enough NVP to sufficiently enhance crosslinking, and having too much NVP so that the mechanical properties start to resemble those of pure crosslinked NVP. Therefore, we propose that there is an optimal window for the amount of NVP added to the prepolymer between 2.0 and 8.0 wt. % NVP.

TABLE 9

Effect of NVP on mechanical properties of elastomers using 5.0 wt. % AIBN at 130° C. for 24 h

| | wt. % | | G | ε | σ | ν | Q |
|---|---|---|---|---|---|---|---|
| elastomer | EG | NVP | (MPa)[a] | (MPa)[a] | (%)[a] | (mmol/L)[a] | (%)[b] |
| 12 | 2 | 0.0 | 1.5 | 0.7 | 65 | 202 | 18 |
| 14 | 2 | 1.0 | 3.3 | 1.3 | 140 | 444 | 18 |
| 15 | 2 | 2.0 | 8.4 | 1.2 | 124 | 1 130 | 19 |
| 16 | 2 | 4.0 | 21.5 | 3.0 | 143 | 2 890 | 24 |
| 17 | 2 | 8.0 | 10.0 | 1.4 | 138 | 1 350 | 21 |
| 18 | 2 | 16.0 | 0.8 | 0.7 | 102 | 108 | 29 |
| 19 | 4 | 0.0 | 0.4 | 0.2 | 80 | 54 | 25 |
| 20 | 4 | 1.0 | 0.4 | 0.2 | 75 | 55 | 32 |
| 21 | 4 | 4.0 | 0.3 | 0.1 | 95 | 40 | 39 |
| 22 | 4 | 16.0 | 0.2 | 0.2 | 110 | 27 | 38 |

[a]Determined by Instron, 20 mm/min crosshead speed
[b]Extracted in methylene chloride for 24 h at 25° C.

As previously discussed, it is advantageous in numerous biomedical applications that the mechanical properties of the device or scaffold be similar to the mechanical properties of the surrounding tissue. Our materials have mechanical properties similar to elastin (which has a Young's modulus of between 0.3 and 0.6 MPa, ultimate stress of 0.36-4.4 MPa and extension at break of 100-220%) (Puskas, J. E.; Chen, Y. Biomacromolecules 2004, 5, 1141).[14] These mechanical properties are similar to elastin rich structures such as ligaments and vascular walls. The ultimate extension of our materials is approaching that of arteries and veins (<220%), and is significantly larger than that of tendons (<18%) (Wang, Y. et al., *Nat. Biotech.* 2002, 20, 602).

Figure 5:
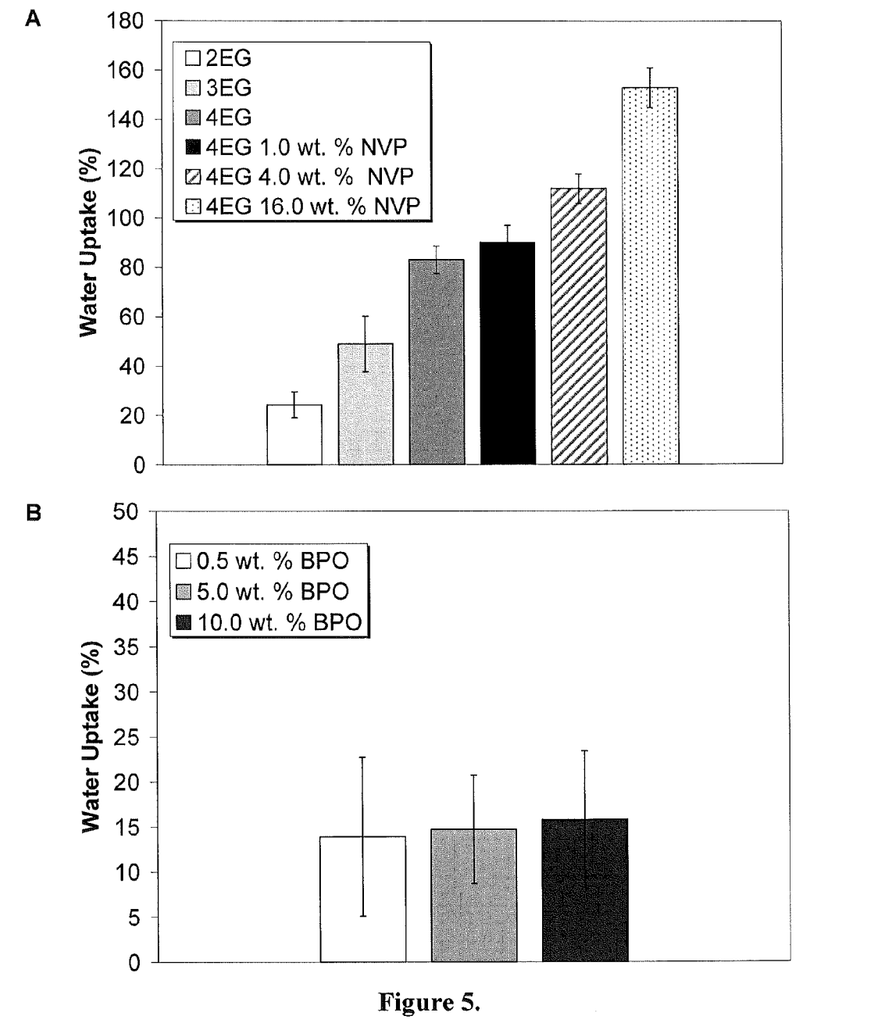
FIG. 5. Variation in the water uptake of elastomers by changing the a) EG length of the prepolymer and amount of NVP additive, and b) concentration of BPO used to crosslink 2EG prepolymers.

Once the ability to tune the thermal and mechanical properties of the materials within a wide range of values was demonstrated, the affect that these modifications had on the water uptake and degradation properties of the elastomers was investigated. It is intuitive that using a longer EG oligomer or more NVP will make the material more hydrophilic, affecting its water uptake properties. The data in FIG. 5 indeed demonstrate that the water uptake properties of the materials differ greatly depending on these variables. Materials prepared from the three different EG oligomer lengths show statistically different water uptake levels, with the level increasing as the EG oligomer length increases. Materials prepared from 4EG show the largest uptake, above 80%, while materials prepared from 2EG show the smallest uptake, near 20%. NVP also affected the water uptake, with HMA:4EG materials with 16.0 wt. % NVP added, demonstrating water uptake levels near 160%, twice that of just HMA:4EG. The effect of initiator concentration on water uptake was also investigated. Water uptake values of Elastomers 1-3 prepared from Prepolymer 1 were nearly identical, even though crosslinking densities increased as the BPO concentration increased (FIG. 5b).

Given the results of the water uptake investigations, differences in the degradation rates are predicted. Degradation investigations were undertaken to confirm these predictions. Just as with the water uptake study, the effect that the EG oligomer length, NVP concentration, and the concentration of BPO used to crosslink the prepolymer had on the degradation of the materials were investigated. The degradation properties were characterized by measuring the loss of mass (FIG. 6) of the elastomers over time.

Figure 6:
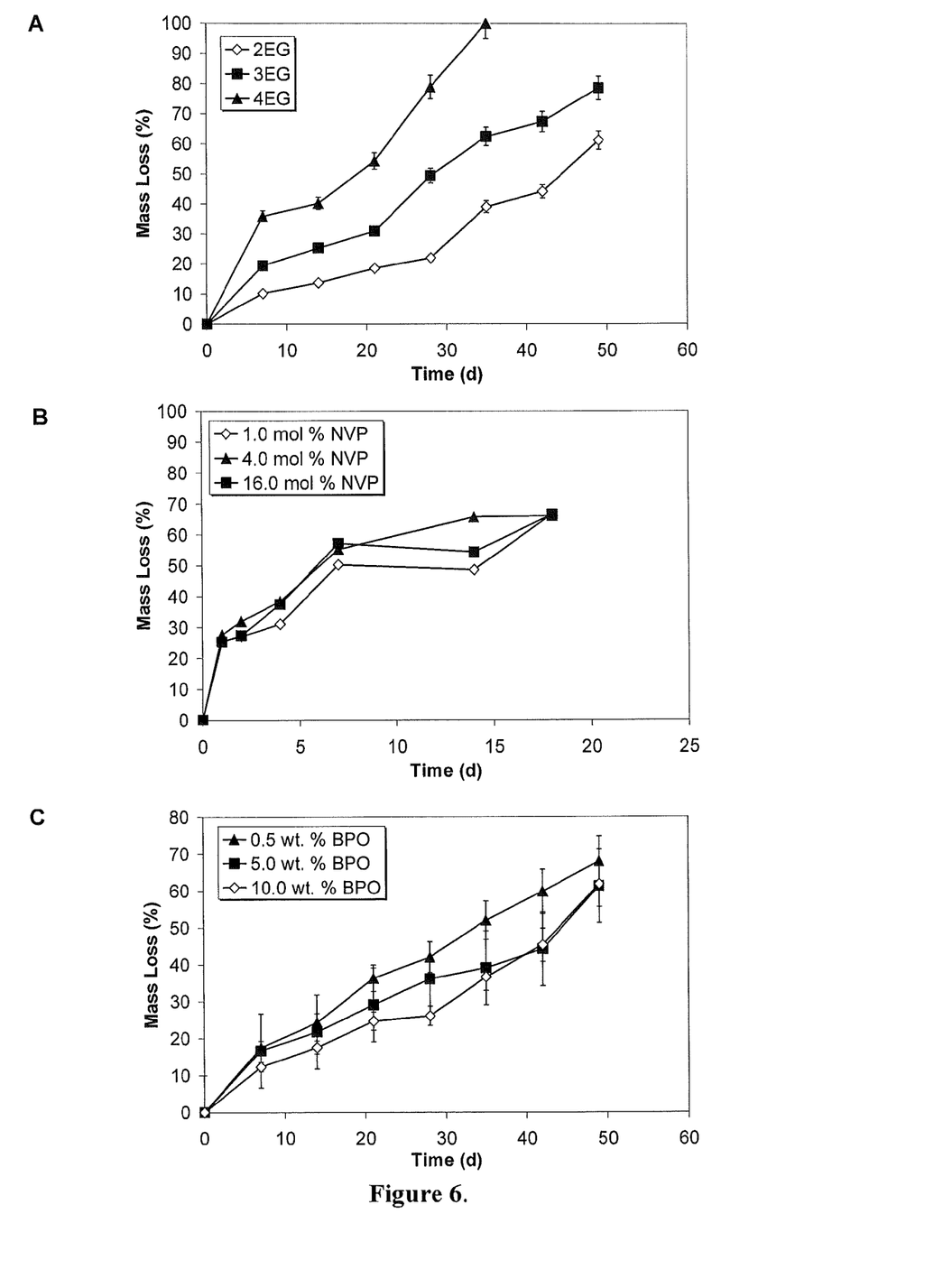
FIG. 6. The effect of the a) EG oligomer length used to prepare the prepolymer b) amount of NVP added and c) concentration of BPO used to crosslink the 2EG prepolymer on the mass loss of the elastomers

Several observations with regard to the mass loss of the elastomers are noted. First, regardless of the EG oligomer or the BPO concentration, all materials demonstrate an initial rapid loss in mass. Following this rapid loss in mass, the rate of mass loss decreases, although to varying degrees. This rapid mass loss can be accounted for by the degradation of the soluble portion of the elastomer. The second observation is that the EG oligomer length has a significant effect on the mass loss of the elastomers (FIG. 6a). The longer the EG oligomer, the larger both the degree and rate of mass loss were (Table 10). Materials prepared from 4EG prepolymers degraded the most rapidly, with complete degradation occurring in 30 days. Third, the addition of NVP has very little effect on the rate of degradation. This marks a significant increase in the rate of degradation compared to similar materials in the literature. Langer provides the most similar example, with materials degrading completely in 60 days. Finally, the concentration of BPO used to prepare the crosslinked elastomers does not have a significant effect on the rate of degradation of the degradable elastomeric materials.

TABLE 10

Rate of mass loss and decrease of Young's modulus of elastomers[a]

| elastomer | $k_{mass} \times 10^{-2}$ (d$^{-1}$) |
|---|---|
| 2EG[b] | 1.8 |
| 3EG[b] | 3.2 |
| 4EG[b] | 5.2 |
| 2EG[c] | 2.2 |
| 2EG[d] | 1.8 |

[a]First order rate determined by plotting ln(loss) v. t and fitting the data with a linear regression excluding the data for the initial rapid mass loss over the first 7 days
[b]5.0 wt. % BPO, 130° C., 24 h
[c]0.5 wt. % BPO, 130° C., 24 h
[d]10.0 wt. % BPO, 130° C., 24 h Finally, given the potential use of these materials for biomedical applications, the cytotoxicity characteristics of these materials were tested. A minimum essential medium (MEM) elution test was performed on homopolymers, copolymers, and epoxidized materials. The materials were extracted with a minimal essential medium for 24 h at physiological conditions. The extracts were then placed on monolayers of L929 mouse fibroblast cells from the ATCC cell line. Materials were scored after 48 h. All homopolymers and copolymers had toxicity scores of 0.0, indicating no cytotoxic response. Crosslinked elastomer materials were also evaluated. The elastomer materials were tested before and after the soluble fraction was removed with methylene chloride. Both scored 0.0, indicating no cytotoxic response.

The foregoing is illustrative of the present invention, and is not to be construed as limiting thereof. The invention is defined by the following claims, with equivalents of the claims to be included therein.

That which is claimed is:

1. A method of making an article comprising a thermoset elastomeric polymer, said method comprising:
    forming an aliphatic polyester prepolymer into said article, and then
    thermally crosslinking said prepolymer to produce said article;
    wherein said aliphatic polyester prepolymer is produced by the process comprising reacting a diol with at least a first diacid, or a diester of said first diacid, to produce said aliphatic polyester prepolymer; wherein said first diacid is a trans-beta-hydromuconic acid (HMA).

2. The method of claim 1, wherein said diol contains at least one ether linkage.

3. The method of claim 1, wherein said diol is further reacted with at a second diacid, or a diester of said second diacid, wherein said second diacid is different from said first diacid.

4. The method of claim 1, wherein said diol is a polyol.

5. The method of claim 1, wherein said diol is a polyol selected from the group consisting of poly(ethylene glycol) and poly(propylene glycol).

6. The method of claim 1, said prepolymer selected from the group consisting of:
    poly(diethylene glycol hydromuconoate);
    poly(triethylene glycol hydromuconoate);
    poly (tetraethylene glycol hydromuconoate); and
    poly(diethylene glycol hydromuconoate-co-diethylene glycol adipate).

7. The method of claim 1, wherein said prepolymer is liquid at a temperature of 25° C.

8. The method of claim 1, wherein said prepolymer is amorphous at a temperature of 25° C.

9. The method of claim 1, said prepolymer further comprising a polymerization initiator.

10. The method of claim 1, said prepolymer further comprising a crosslinking agent.

11. The method of claim 1, said prepolymer further comprising an active agent.

12. The method of claim 1, wherein said article has a Young's modulus of not less than 0.02 MPa.

13. The method of claim 1, wherein said article is a biomedical implant.

14. The method of claim 1, wherein said article is a drug depot.

15. The method of claim 1, wherein said article is a drug eluting stent.

16. The method of claim 1, wherein said article is a tissue engineering scaffold.

17. A method of making an article comprising a thermoset elastomeric polymer, said method comprising:

forming an aliphatic polyester prepolymer into said article, and then thermally crosslinking said prepolymer to produce said article; wherein:

said aliphatic polyester prepolymer is produced by the process comprising reacting a diol with at least a first diacid, or a diester of said first diacid, to produce said aliphatic polyester prepolymer; wherein said first diacid is a trans-beta-hydromuconic acid (HMA);

said diol is a polyol selected from the group consisting of poly(ethylene glycol) and poly(propylene glycol);

said prepolymer is liquid and amorphous at a temperature of 25° C.; and said article has a Young's modulus of not less than 0.02 MPa.

* * * * *